United States Patent [19]

Schwartz

[11] Patent Number: 4,767,206
[45] Date of Patent: Aug. 30, 1988

[54] CALIBRATION METHOD FOR FLOW CYTOMETRY USING FLUORESCENT MICROBEADS AND SYNTHESIS THEREOF

[75] Inventor: Abraham Schwartz, Durham, N.C.

[73] Assignee: Flow Cytometry Standards Corporation, Research Triangle Park, N.C.

[21] Appl. No.: 685,464

[22] Filed: Dec. 24, 1984

[51] Int. Cl.[4] .............................................. G01N 21/64
[52] U.S. Cl. .................... 356/73; 250/461.2; 436/10; 436/172; 356/39; 356/243
[58] Field of Search .................... 356/39, 73, 243, 72; 436/10, 172; 422/55, 68; 523/201, 223; 250/252.1, 459.1, 461.2, 458.1; 377/10–12, 29; 364/555, 571; 209/3.1, 3.3

[56] References Cited

U.S. PATENT DOCUMENTS

| | | | |
|---|---|---|---|
| 4,157,323 | 3/1986 | Yen et al. | 522/84 |
| 4,162,282 | 7/1979 | Fulwyler et al. | 436/10 X |
| 4,225,783 | 9/1980 | Palin et al. | 356/39 X |
| 4,247,434 | 1/1981 | Vanderhoff | 523/223 |
| 4,285,819 | 8/1981 | Yen et al. | 210/679 |
| 4,326,008 | 4/1982 | Rembaum | 428/403 |
| 4,336,173 | 1/1982 | Ugelstad | 523/221 X |
| 4,499,052 | 2/1985 | Fulwyler | 436/172 X |

Primary Examiner—R. A. Rosenberger
Attorney, Agent, or Firm—Steven J. Hultquist

[57] ABSTRACT

A method of calibrating a flow cytometer is based on a set of highly uniform microbeads associated with a fluorescent dye in such a way that the microbeads have the same excitation and emission spectral properties as the samples which are to be measured. The calibration values of the microbeads are plotted against the relative fluorescence intensity peak channel for each microbead in the set. From this calibration plot, the relative fluorescence intensity peak channel of the sample is translated into equivalent soluble fluorescent dye molecules per sample particle. The calibration values of the standard microbeads are determined against solutions of the dyes. In cases where the background scatter of the bulk microbeads suspensions is too high for a direct determination against the solutions, a different set of microbeads with low background scatter is calibrated against the dye solutions and used to make an initial calibration of the flow cytometer, which in turn, is used to calibrate the uniform microbead standards. A novel method of making the microbead standards is also disclosed.

3 Claims, 4 Drawing Sheets

CALIBRATION METHOD FOR FLOW CYTOMETRY USING FLUORESCENT MICROBEADS AND SYNTHESIS THEREOF

TECHNICAL FIELD

The invention relates to uniform fluorescent particles used to align and calibrate flow cytometric instruments. More specifically, the invention relates to the synthesis and calibration of uniform polymeric fluorescent microbeads.

BACKGROUND ART AND REFERENCE DESCRIPTION

Flow cytometry is the process of analyzing and sorting cells in a flowing stream. This is accomplished by intersecting the stream with an incident light, usually a laser, and detecting the resulting scattered light and fluorescence of the individual cells as a function of the particular physical characteristics or attached fluorescent dye, respectively. In addition, electronic volume sensing has also been incorporated in some flow cytometry instruments. With this array of detectors, sub-populations of cells can be analyzed and sorted in arbitrary terms by just detecting their qualitative differences. However, without size and fluorescent standards, no quantitative information on the individual cells can be gained other than the number of them counted and their proportion relative to the rest of the sample.

To determine quantitative differences between sub-populations of cells, and moreover, to give individual populations a quantitative relevance, standards are necessary with known amounts of fluorescence to which these cell samples can be compared. In FIG. 1, a microbead containing a fluorescent dye, fluorescein isothiocynate (FITC), is shown along with a cell labeled with the same dye. If a series of such microbeads containing varying amounts of the fluorescent dye is run on a flow cytometer, the resulting distributions will be obtained, as shown in FIG. 2, indicated by "Bead 1, Bead 2, and Bead 3". Now if a cell population stained with the same dye is also run on the flow cytometer under the same conditions, then the fluorescence intensity of the cells can be quantitatively compared to those of the calibrated microbeads.

Various fluorescent particles have been used in conjunction with flow cytometry including fixed cells, pollen, fluorescent microbeads, and stained nuclei. However, their use has been limited for the most part to instrument alignment and size calibration. Quantitation of fluorescence intensity of cell samples has been hampered by not having a highly uniform, stable particle which has the same excitation and emission spectra as the cells being measured. Those particles which contain the proper dyes, e.g., the fluorescein stained nuclei (marketed as Fluorotrol-GF by Ortho Diagnostic Systems, Inc.) are not stable over long periods of time and those which are considered stable, e.g., the microbeads, have not contained the same dyes which label the cells. Highly uniform fluorescent microbeads have been available from various sources for a number of years. However, none of these beads have been suitable as quantitative standards for flow cytometry instruments because (1) many of these fluorescent microbeads are smaller than the cells to be analyzed and (2) the fluorescent dyes which have been incorporated into the small microbeads are different from those attached to the cells. Attempts have been made to cross-calibrate microbeads containing one dye against solutions or cells containing a different dye, e.g., cumerin containing microbeads against fluorescein solutions. However, such a calibration is only good for the one excitation and emission filter system. Use of slightly different filter systems, which may occur with instruments from different manufacturers, can significantly alter the quantitative results. The invention recognizes that the key to having a useful fluorescent standard which can be used on any instrument or filter system is for the microbead to have the same excitation and emission spectra as the sample. A more subtle point recognized by the invention is that the environment of the dye molecules can have a large effect on the fluorescence spectra. This is demonstrated in FIG. 3, where the emission intensity of a cell labeled with fluorescein is compared to that of microbeads with fluorescein on the surface and fluorescein within the body of the hydrophobic microbead. The surface fluorescenated microbead has the fluorescein in contact with the aqueous medium, and has the same emission properties as a function of wavelength as does the fluorescein labeled cell suspended in an aqueous medium, whereas, the microbead with the fluorescein within the hydrophobic bead body has a very different response because both the excitation and emission spectra have shifted and broadened as a function of the dye being in a hydrophobic medium and not in contact with water. The related spectra as recognized by the invention are shown in FIG. 4. Recently, larger microbeads suitable for size calibration of biological cells have been synthesized in outer space (see NASA TM 78132 "Large-size Monodisperse Latexes as a Commercial Space Product", and U.S. Pat. No. 4,247,434), as well as, in the laboratory (see U.S. Pat. No. 4,336,173). However, none of these large microbeads were reported to contain a fluorescent dye. Moreover, synthesis as described in U.S. Pat. No. 4,336,173 was found to be hampered by agglomeration and high doublet formation. Even with the suggested polymeric stabilizers, the yields of mono-dispersed microbeads were lower than acceptable. The present invention has for its object the accomplishment of this task. Other objects will appear as the description proceeds.

DISCLOSURE OF INVENTION

The present invention is based on the synthesis and calibration of a set of highly-uniform, polymeric microbead standards. The microbead standards are used to align and calibrate flow cytometers over the size and fluorescence range of interest. The fluorescent microbeads of the invention exhibit excitation and emission spectra equivalent to those of the samples being measured. The calibration of fluorescence intensity of the microbeads is in terms of number of equivalent soluble fluorescent molecules per microbead.

BEST MODE FOR CARRYING OUT THE INVENTION

Synthesis of the Microbeads

The synthesis of large-sized microbeads (3–9 microns in diameter) is accomplished according to the invention by swelling seed microbeads with two or more substances. The swelling is such that as prescribed by thermodynamics, the enthropy of mixing within the seed microbead allows the seed to swell many times over the amount the seed would swell if mixed with a single substance. While this general approach has been previously described in U.S. Pat. No. 4,336,173, further improvements are critically needed with regard to the stability of the systems and examples described in such patent. Microbeads with less tendency to agglomerate and with less tendency to form doublets are needed. The present invention thus seeks to provide a more satisfactory stability and other improved characteristics in the microbeads.

In the present invention, high concentrations of the oil soluble initiator are dissolved in the oil soluble monomers. This solution is then homogenized with an aqueous surfactant solution prior to using it to swell the microbeads already containing an oil soluble substance. In addition, the invention system is stabilized with alkaline halide salts, preferably potassium chloride, to keep the seeds separated during swelling and polymerization. Once swollen, the suspension is purged with nitrogen and heated to initiate polymerization. It was discovered that the high concentrations of oil soluble initiator (0.5-5%) caused such rapid polymerization within the swollen seeds, that polymerization of monomer in the aqueous phase could not proceed far enough to cause agglutination. It was further observed that any monomer/initiator droplets which were not taken up by the seeds would polymerize individually, since they contained initiator, forming a second smaller population of microbeads and again avoiding agglutination of the other microbeads, especially since the system was stabilized by the addition of salt. Yields of the large-sized monodispersed microbeads were above 95 percent.

Microbead Fluorescenation

Figure 8:
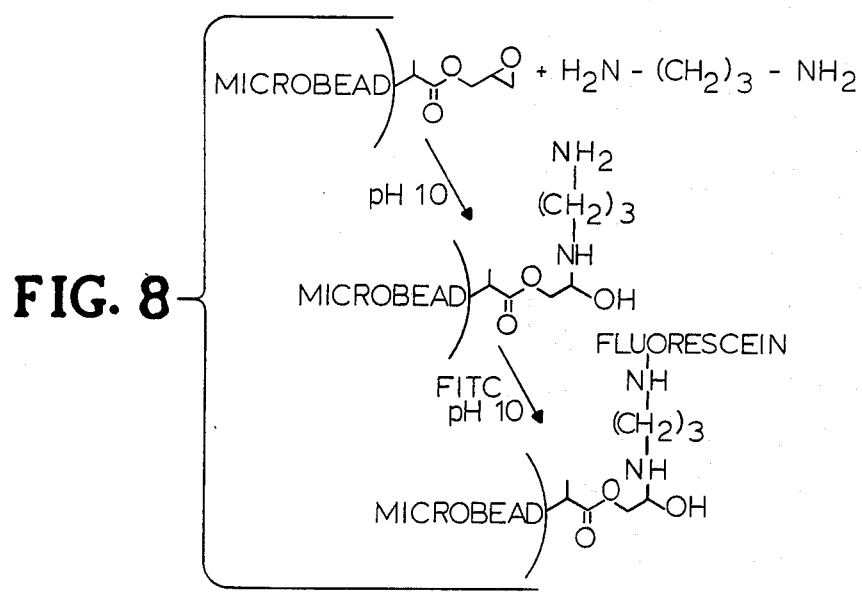
FIG. 8 illustrates microbead surface fluorescenation.
Figure 5:
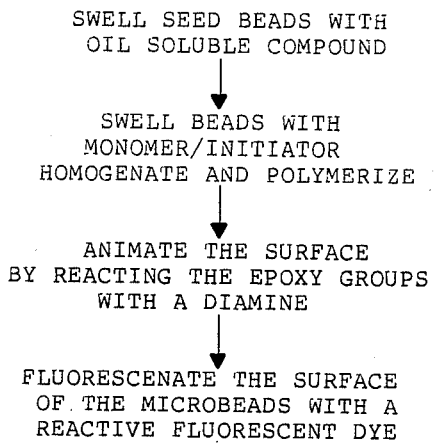
FIG. 5 is a block diagram illustrating the steps for synthesizing the microbeads of the invention.
Figure 6:
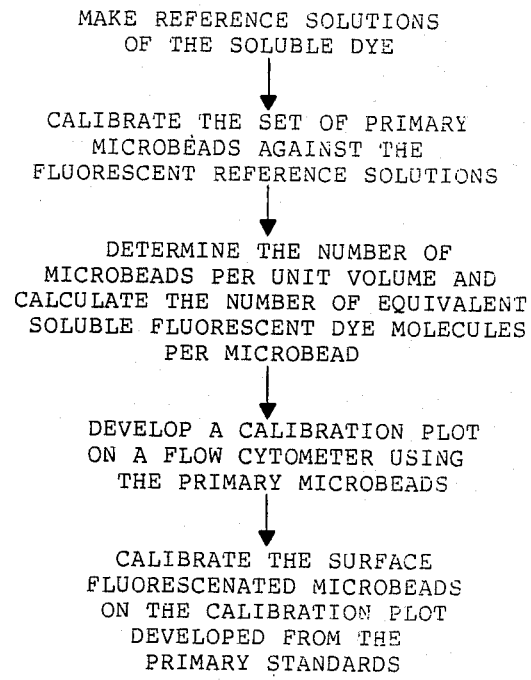
FIG. 6 is a block diagram of the steps involved in calibrating the fluorescent microbeads of the invention.
Figure 7:
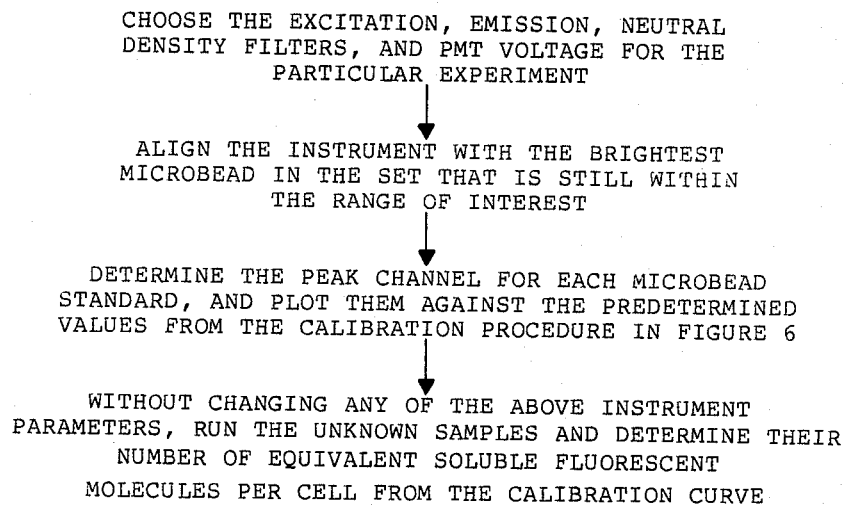
FIG. 7 is a block diagram illustrating calibration of an instrument utilizing the invention microbeads.

Although fluorescent dyes can be copolymerized into the invention microbead, such microbeads may not be useful as fluorescent standards. This is so because incorporation into a non-aqueous environment can cause spectral shifts in the dye. Such spectral shifts would render the microbead near worthless as quantitative fluorescence standards. To be useful as a fluorescent standard, the microbeads have to have a functionality on their surface by which the fluorescent dye molecules can be attached. This arrangement maintains the fluorescent dye in the same aqueous environment as that of the cells labeled with the dye, thus retaining equivalent spectra. The preferred functional group on the surface of the large microbead is the epoxy group. It has versatility, in that it can be directly activated under mild conditions, pH 8.5-10, to covalently link with amine-containing dyes, e.g., fluorescein amine or phycoeyrthrine, or it can be linked to a spacer group, e.g., 1,3-diaminopropane or 1,6-diaminohexame which in turn can be linked to a reactive dye, e.g. fluorescein isothiocynate (FITC), under similar mild conditions, pH 8.5-10, to ensure that the dye is surrounded by the aqueous medium. This scheme is illustrated in FIG. 8.

Calibration of the Fluorescent Microbead Standards

Some researchers have attempted to calibrate fluorescent microbeads as well as proteins with radioactive labels in terms of absolute numbers of dye molecules. This approach results in a quagmire of correction factors involving quenching considerations and change in extinction coefficients due to the chemical conjugation of the dye. These problems are reflected by the fact that there are as of yet no NBS accepted primary fluorescent standards for quantitative intensity, let alone for those specific fluorescent dyes of interest in flow cytometry.

Although the idea of quantitation in terms of absolute numbers of molecules of a fluorescent dye is attractive, its practicality at this time is unobtainable. Therefore, an alternative calibration system is provided by means of the present invention which relate a microbead standard back to a stable and reproducible solution of primary standard which has the same excitation and emission spectra as the sample being measured. With sufficiently dilute solutions, considerations of quenching and changes of extinction coefficient may be avoided, as long as the spectra of the primary soluble standard solution, the microbead standards, and the labeled cells in the sample are the same. Thus, fluorescent intensities of a sample may be related to a quantitative concentration of a soluble primary standard via calibrated microbeads which have the same spectra.

The fluorescenated microbeads are calibrated with such a system in terms of Equivalent Soluble Dye Molecules per Microbead. For example, fluorescein microbeads are standardized against a primary laser grade fluorescein. Laser grade fluorescein was chosen because it is the most stable, and of the highest purity, of any of the fluorescein compounds. Also, it has excitation and emission spectra equivalent to that of FITC-labeled cells and the fluorescein microbead standards.

Figure 10:
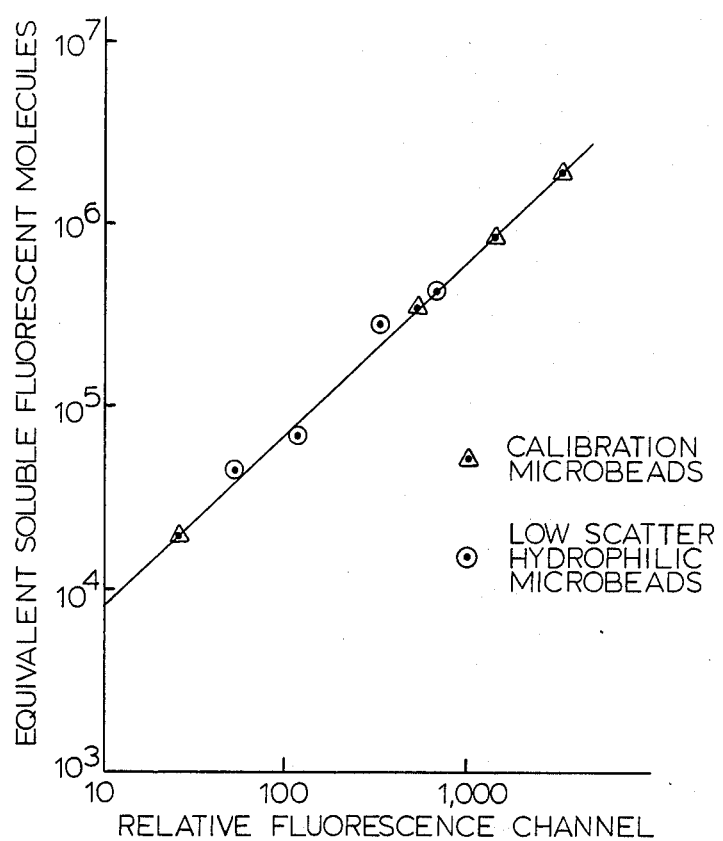
FIG. 10 is a plot on logarithmic scale of Equivalent Soluble Fluorescent Molecules versus Relative Fluorescent Channel.

The fluorescent microbead standards are calibrated by determining the fluorescent intensity of standard solutions of laser grade dyes with a fluorometer and relating those fluorescence intensities to the fluorescence intensity of suspensions of the microbeads. The number of microbeads in the suspension per unit volume is determined with a Coulter Counter TM or a Hemocytometer TM. Then from these data, the number of equivalent soluble dye molecules per microbead is calculated by dividing the equivalent soluble dye molecules per unit volume by the number of microbeads per that unit volume. In the actual practice of calibrating the fluorescent microbead standards, the refractive index of the blank beads (those unfluorescenated) is too high which causes high background scatter (250,000 equivalent soluble dye molecules per microbead). This makes it impossible to directly calibrate them in bulk suspension in a fluorometer. In this case, a different primary microbead whose scatter from the blank microbead is low (1000 equivalent soluble dye molecules per microbead) must be used for calibration against the dye solutions. Such primary microbeads may be synthesized from hydrophillic monomers as 2-hydroxy ethyl methacrylate, methacrylic acid acrylamide, and allyl fluorescein as described in U.S. Pat. Nos. 4,157,323; 4,285,819 and 4,326,008. These primary microbeads are then used to calibrate the flourescence channels of a flow cytometer, and in turn the original flourescent microbead standards are calibrated against the plot developed with the primary microbeads as shown in FIG. 10. These primary microbeads are themselves not as useful as the standard microbeads because they are too small (0.5-1.0 microns), and are not very uniform.

Synthesis of Microbeads

Example 1

One milliliter of 1-chlorododecane (CDD) was homogenized with 2.5 ml of 0.25% sodium dodecyl sulfate (SDS) in water and this was added to 5 ml of 10% suspension of 2.02 micron polyvinyl toluene microbeads in 20 ml of SDS solution. Ten milliliters of 30% acetone in water was added to help incorporate the CDD into the microbeads. This was stirred for 12 hours before 1 ml of the suspension was added to 10 ml of distilled water and 20 ml of SDS and evacuated to remove the acetone. Two hundred milligrams of benzoyl peroxide initiator was dissolved in a 5 ml solution of 95% methyl methacrylate and 5% glycidyl methacrylate before it was homogenized with an equal volume of 0.25% SDS solution. The ten milliliters of the homogenate was then added to the above evacuated suspension of swollen seed microbeads and the suspension was purged with nitrogen and heated to 70° C. for two hours to cause rapid polymerization of the swollen microbeads. The result was a highly uniform microbead with a diameter of 5.3 microns. The yield was 96 percent.

EXAMPLE 2

The procedure was the same as in Example 1, with the exception that 20 ml of homogenized monomers and initiator was added to the seed suspension resulting in microbeads 8.7 microns in diameter.

FLUORESCENATION

Example 3

The microbeads in Examples 1 and 2 were washed in 0.25% SDS solution and to them was added an equal volume of 10% 1.3-diaminopropane adjusted to pH 10.0. This was stirred for 12 hours then washed in SDS solution three times and in 0.1M NaHCO$_3$, pH 8.5 two times. FITC was added to portions of these aminated suspensions and then they were washed four times in 0.05M phosphate buffer pH 7.2. This resulted in green fluorescent microbeads as viewed in an epiluminescent fluorescent microscope.

Example 4

The same procedures was used as in Example 3, except Texas Red was used to replace FITC. The result was red fluorescent microbeads as viewed under the fluorescence microscope.

Example 5

The microbeads obtained in Examples 1 and 2, still containing functional epoxy groups, were mixed with a solution of phycoerytherine at a pH of 9.5 for 12 hours. After washing the resulting microbead had a red fluorescence under the fluorescence microscope.

Example 6

The same procedure was carried out as in Example 5, except the microbeads were added to a solution of DNA. Following washing in PBS pH 7.2, the microbeads coated with DNA were exposed to propidium iodide and the microbeads had a red fluoresence under the fluorescence microscope.

Example 7

Figure 9:
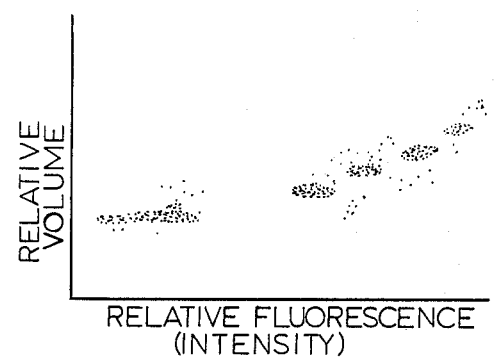
FIG. 9 is a dot plot of a set of five calibration microbeads with varying size and fluorescence intensities.

The microbeads in Example 3 were fluorescenated at predetermined levels of fluorescence intensity with FITC and/or Texas Red by introducing small amounts of the dyes stepwise into the microbead suspensions and checking the microbeads fluorescence intensity with a flow cytometer at each step to check if the resulting microbeads had fluorescent intensities equivalent to each step. Specifically, 1 mg of FITC was dissolved in 3 ml of methanol and this was added dropwise to a suspension of microbeads from Example 1 in 0.1M NaHCO$_3$ at pH 8.5 while intermittently determining the fluorescence level with a flow cytometer. Only enough FITC methanol solution was added to the microbeads to reach the desired microbead fluorescence intensity. Other suspension of the same microbeads were brought to different levels of intensity resulting in a set of microbeads of various specific predetermined fluorescence levels, i.e., $2\times 10^4, 4\times 10^5, 9\times 10^5$ and $2\times 10^6$, which can be used to develop a calibration curve for a flow cytometer as seen in FIGS. 9 and 10.

CALIBRATION

Example 8

Step 1

Excitation and emission spectra were taken in PBS pH 7.2 of soluble laser grade fluorescein, hydrophillic (low background scatter) 1 micron microbeads, and the microbeads from Example 4. All the excitation spectra of these samples had a peak at 293 (matched within 3 nanometers) and had equivalent shapes. They also had matching emission spectra with the peak at 518 nanometers.

Step 2

In 1000 mls. of PBS pH 7.2, 9.6 mgs of laser grade fluorescein was dissolved and further diluted 1:100 making a solution of $4.8\times 10^{-8}$M fluorescein. The fluorescence intensity of this solution was read in a fluorometer and then ratioed against the readings of dilute microbead suspensions (1 million microbeads per ml) to determine the equivalent fluorescein molarity of the microbead suspensions. This molarity was divided by the number of microbeads per ml (1.4 million per ml) as determined with a Hemocytometer. The $7.8\times 10^5$ soluble fluorescein molecules per microbead.

Step 3

A set of the small calibrated hydrophillic microbeads were run on a flow cytometer and a calibration plot was made of the microbead fluorescence intensity versus the instrument fluorescent channel number. This calibration curve was then used in turn to quantitate the fluorescence intensity in terms of equivalent soluble fluorescein molecules per microbead of the set of microbeads in Example 7.

To summarize various aspects of the invention, the invention provides a method by which a flow cytometer may be calibrated in terms of the number of equivalent soluble fluorescent dye molecules per fluorescence intensity channel of the instrument by the use of highly uniform microbeads with a fluorescent dye associated therewith, such that the microbeads have the same excitation and emission spectra as samples being measured. The invention method is thus based on the microbeads themselves being calibrated in terms of equivalent numbers of soluble fluorescent dye molecules per microbead. Stated differently, the invention method of calibrating the microbeads is based on determining the number of equivalent soluble fluorescent dye molecules necessary to give rise to the same level of fluorescence intensity as the particular microbead. This is accomplished by determining the fluorescence intensity of a suspension of microbeads with a fluorometer as compared to solutions of the free fluorescent dye, and dividing by the number of microbeads in the suspension to yield the number of equivalent soluble fluorescent dye molecules per microbead. When background scatter of these microbeads is too high for direct calibration, a second type of low background scatter hydrophilic microbead is calibrated against the dye solutions and these low background scatter microbeads are then calibrated against the hydrophilic microbeads.

The flow cytometery calibration microbeads useful for the invention have the following properties:

(a) They are highly uniform and in the size range of the sample cells which are being measured, 1–15 $\mu$ in diameter, preferably 3–10 $\mu$ in diameter.

(b) They have associated with them a fluorescent dye that will give rise to the same excitation and emission spectra as that of the cell sample which is being measured.

(c) They have fluorescence intensities between $10^3$–$10^7$ equivalent soluble molecules of fluorescent dye per microbead.

(d) They are stable with respect to size and fluorescence intensity in their suspending media, which in turn is the same as that in which the cell samples are suspended.

The calibration microbeads are composed of hydrophobic polymeric materials which have chemically functional groups on the surface of the microbeads such that a fluorescent dye may be conjugated via a stable bond, and such that this bonding will maintain the fluorescent dye in contact with the suspension medium. The hydrophobic polymeric materials are preferably a copolymer of 95% methyl methacrylate and 5% glycidyl methacrylate, but the composition could include copolymers in various ratios of styrene, vinyl toluene, and other acrylate and methacrylate esters with glycidyl methacrylate, allyl glycidyl ether, or other epoxy containing monomers.

The preferred method of making the calibration, microbead standard is to first swell seed beads with an oil soluble compound, then following with a second swelling with a aqueous homogenate which contains a monomer with a high concentration of oil soluble initiator (1–5%) dissolved in it, which will cause polymerization at such a rapid rate in the oil (monomer) phase as to minimize any polymerization in the aqueous phase, thus reducing agglomeration of the microbeads.

The preferred linkage to the microbeads of the fluorescent dye is through a covalent linkage which can be generated by first animating the surface of the microbeads with a diamine, preferably 1,3-diaminopropane or 1,6-diaminohexane, through reacting with the epoxy surface group, then reacting the aminated surface of the microbeads with a reactive fluorescent dye, such as fluorescein isothiocynate or Texas Red. However, a stable linkage can be directly formed to the microbead via the epoxy group reacting directly to a primary amine on the fluorescent dye, such as fluorescein amine.

Also to be noted is that sensitivity of the flow cytometer can be determined by using the microbead with the lowest level of fluorescence and a blank microbead, i.e. a microbead without an attached fluorescent molecule, in such a way as to determine the distance between fluorescent peaks of the two microbeads being employed for such purpose.

From the foregoing, it can be seen that the invention not only provides a unique method for calibrating a flow cytometer but also a unique synthesis of the microbead standards related thereto.

What is claimed is:

1. The method of establishing a standard reference for calibrating a flow cytometer, comprising the steps of:
   (a) making up a first batch of microbeads to serve as standard microbeads, each said standard microbead comprising:
      (i) a highly-uniform sized body substantially within the range of 3 to 15 microns in size, formed of hydrophobic polymeric material; and
      (ii) fluorescent dye material covalently bonded to the surface of said body material via chemical functional groups and in such manner that the fluorescent spectra thereof remains unaltered;
   (b) making up a second batch of microbeads to serve as primary microbeads, each said primary microbead comprising:
      (i) a hydrophilic polymeric material; and
      (ii) a fluorescent dye copolymerized within the microbead and made up of a material allowing free access of aqueous media throughout the microbead, and having a fluorescent spectra that remains unaltered after said copolymerization;
   (c) determining that the excitation-emission spectra of the microbeads of both batches are substantially identical to each other, substantially identical to the same free dye when in the same suspending solution and also substantially identical to a particle sample such as cells having the same known dye incorporated therein;
   (d) based on the identities in step (c) being established, calibrating said second batch of microbeads against a sample of said free dye to determine the equivalent soluble fluorescent molecules per microbead;
   (e) developing a calibration curve for said second batch of microbeads representing equivalent soluble fluorescent molecules per relative fluorescent channel of a flow cytometer; and
   (f) measuring the fluorescent intensities of the highly uniform microbeads of said first batch with a flow cytometer to determine the relative fluorescent channel thereof and thereafter determining from step (e) the number of equivalent soluble fluorescent molecules per microbead in said first batch, thereby establishing said first batch of microbeads as a standard reference.

2. A method for calibrating a flow cytometer for measuring cell and other particle samples, comprising the steps of:
   (a) preparing microbeads with a fluorescent dye associated therewith in a manner such that the microbeads have the same excitation and emission spectra as the samples being measured, said microbeads comprising a first batch of hydrophobic microbeads having a fluorescent dye material covalently bonded to their surfaces, and a second batch of low background scatter hydrophilic microbeads having a fluorescent dye copolymerized within the microbeads and made up of a material allowing free access of aqueous media throughout the hydrophilic microbeads;
   (b) calibrating said low background scatter hydrophilic microbeads against solutions of the free fluorescent dye, by the steps comprising:
      (i) determining that the hydrophilic microbeads in the same suspending solution have an excitation-emission spectra substantially identical to solutions of the free dye;
      (ii) determining the fluorescent intensity of a suspension of said hydrophilic microbeads with a fluorometer as compared to solutions of the free fluorescent dye, to determine the number of equivalent soluble dye molecules per unit volume of the hydrophilic microbead suspension;
      (iii) determining the number of microbeads per unit volume of the hydrophilic microbead suspension; and
      (iv) dividing the equivalent soluble dye molecules per unit volume of the hydrophilic microbeads suspension by the number of microbeads per unit volume of the hydrophilic microbeads suspension to yield the number of equivalent soluble fluorescent dye molecules per hydrophilic microbead;
   (c) calibrating the hydrophobic microbeads in terms of equivalent numbers of soluble fluorescent dye molecules per microbead, by measuring the fluorescent intensities of the highly uniform hydrophilic microbeads to determine the relative fluorescent channel thereof and thereafter determining from step (b) (iv) the number of equivalent soluble fluorescent molecules per microbead in said hydrophilic microbeads, thereby establishing said hydrophilic microbeads as a standard reference; and
   (d) calibrating the flow cytometer in terms of the number of equivalent soluble fluorescent dye molecules per fluorescent intensity channel of the cytometer by the use of said hydrophobic microbeads.

3. A method for calibrating a flow cytometer for measuring cell particle samples, comprising the steps of:
   (a) preparing uniform microbeads with a fluorescent dye associated therewith in a manner such that the microbeads have the same excitation and emission spectra as the samples being measured;
   (b) determining the number of equivalent soluble fluorescent dye molecules necessary to give rise to the same level of fluorescence intensity as said microbeads, by the steps of:
      (i) determining the fluorescence intensity of a suspension of said microbeads with a fluorometer as compared to solutions of the free fluorescent dye, to determine the number of equivalent soluble dye molecules per unit volume of said suspension of microbeads;
      (ii) determining the number of microbeads per unit volume in said suspension thereof; and
      (iii) dividing the number of equivalent soluble dye molecules per unit volume of said suspension of microbeads by the number of microbeads per unit volume of the suspension to yield the number of equivalent soluble fluorescent dye molecules per microbead;
   (c) for microbeads of known number of equivalent soluble fluorescent dye molecules per microbead as determined from step (b)(iii), determining the peak fluorescence intensity channel of the flow cytometer for said microbeads;
   (d) constructing a calibration plot of the number of equivalent soluble fluorescent dye molecules as a function of the peak of fluorescence intensity channel of the flow cytometer for said microbeads whose peak fluorescence intensity channels wee determined in step (c);
whereby at the same instrument parameters as employed to establish said calibration plot, the peak fluorescence intensity channel of said cell or particle sample is measured on the flow cytometer, and from such peak fluorescence intensity channel value, the number of equivalent soluble fluorescence dye molecules in said sample is determined from said calibration plot.

* * * * *

UNITED STATES PATENT AND TRADEMARK OFFICE
CERTIFICATE OF CORRECTION

Figure 1:
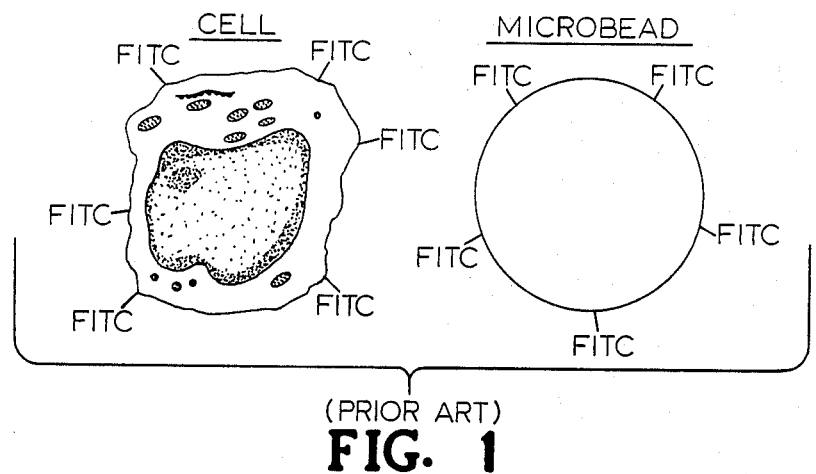
FIG. 1 schematically illustrates a microbead containing a fluorescent dye compared with a cell labelled with the same dye.
Figure 2:
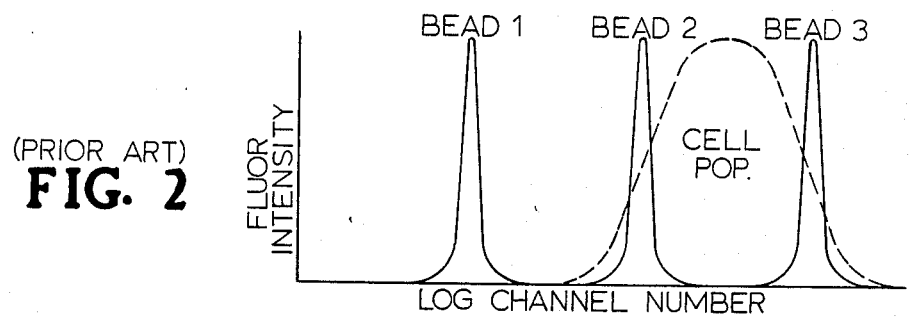
FIG. 2 illustrates the fluorescent intensity distribution of several microbeads run on a flow cytometer.
Figure 4:
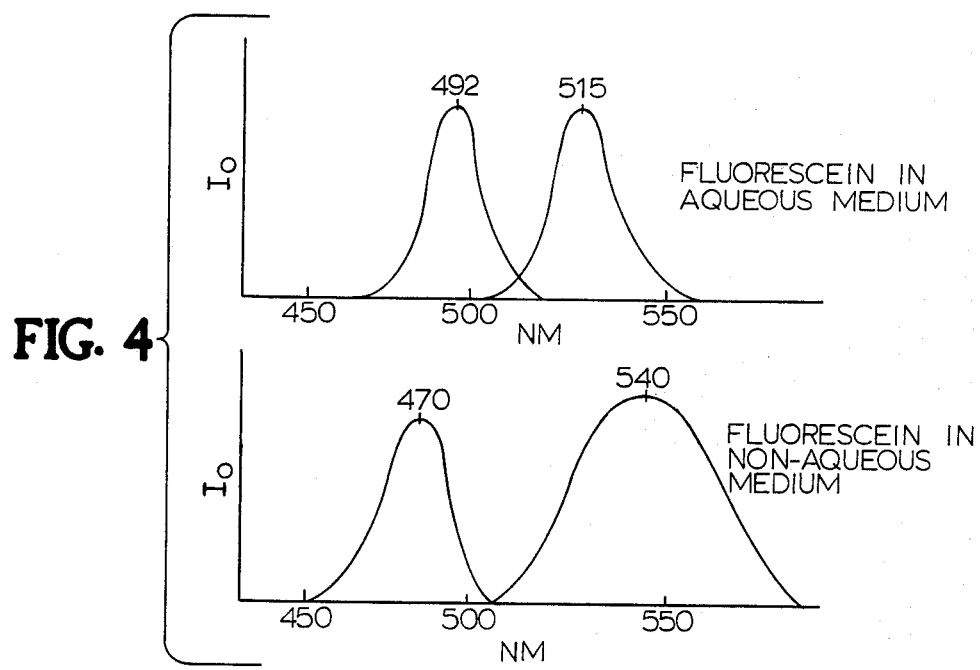
FIG. 4 compares the spectra of fluorescein loaded microbeads in an aqueous medium compared with being in a non-aqueous medium.
Figure 3:
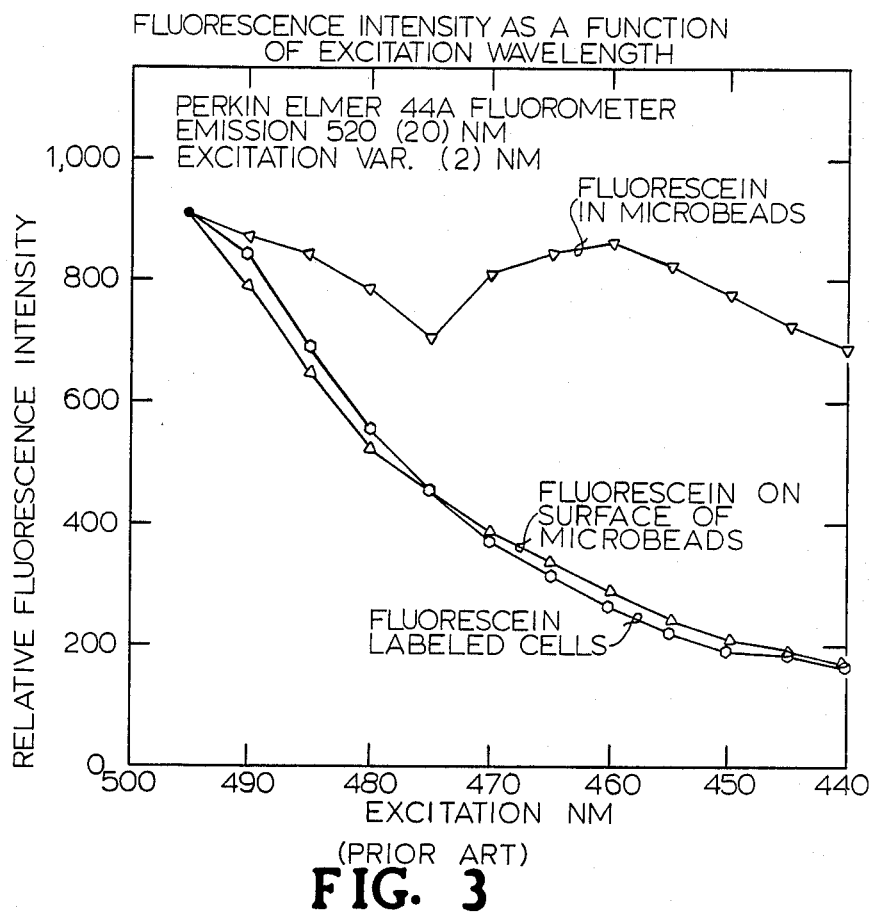
FIG. 3 illustrates a comparison of emission intensity of a fluorescein labelled all with microbeads having fluorescein on the surface and with other microbeads having fluorescein within the body of the microbead.

PATENT NO.   : 4,767,206
DATED        : August 30, 1988
INVENTOR(S)  : Abraham Schwartz It is certified that error appears in the above-identified patent and that said Letters Patent is hereby corrected as shown below:

In Figure 3, delete the legend --(PRIOR ART)--.

Column 10, line 41, change "wee" to --were--.

Signed and Sealed this

Twenty-fourth Day of January, 1989

Attest:

DONALD J. QUIGG

*Attesting Officer*     *Commissioner of Patents and Trademarks*